: US 7,774,324 B1
(45) Date of Patent: Aug. 10, 2010

(12) United States Patent
Henderson et al.

(54) PROGRESS-TRACKING SERVICE

(75) Inventors: Kenneth Henderson, Folsom, CA (US); Steven A. Sholtis, El Dorado Hills, CA (US)

(73) Assignee: Intuit Inc., Mountain View, CA (US)

( * ) Notice: Subject to any disclaimer, the term of this patent is extended or adjusted under 35 U.S.C. 154(b) by 347 days.

(21) Appl. No.: 11/888,104

(22) Filed: Jul. 31, 2007

(51) Int. Cl.
*G06F 7/00* (2006.01)
(52) U.S. Cl. .................. 707/701; 707/729; 707/805; 705/2; 705/4; 705/9
(58) Field of Classification Search ............... 707/1–3, 707/100–102, 200, 701, 729, 805; 705/2, 705/4, 9
See application file for complete search history.

(56) References Cited

U.S. PATENT DOCUMENTS

| 5,786,814 | A  | * | 7/1998  | Moran et al. ......... 707/E17.028 |
| 5,826,237 | A  | * | 10/1998 | Macrae et al. ................. 705/2 |
| 6,208,974 | B1 | * | 3/2001  | Campbell et al. .............. 705/3 |
| 2003/0028399 | A1 | * | 2/2003  | Davis et al. .................... 705/2 |
| 2003/0038831 | A1 | * | 2/2003  | Engelfriet ................... 345/719 |
| 2003/0229522 | A1 | * | 12/2003 | Thompson et al. ............. 705/4 |
| 2004/0247748 | A1 | * | 12/2004 | Bronkema .................. 426/106 |
| 2006/0089862 | A1 | * | 4/2006  | Anandarao et al. ............. 705/4 |
| 2006/0235738 | A1 | * | 10/2006 | Doyle et al. .................... 705/9 |
| 2007/0244777 | A1 | * | 10/2007 | Torre et al. .................... 705/35 |
| 2007/0250352 | A1 | * | 10/2007 | Tawil ............................. 705/4 |
| 2008/0015892 | A1 | * | 1/2008  | Gowdy et al. .................. 705/2 |
| 2008/0052001 | A1 | * | 2/2008  | Bodin et al. .................... 702/1 |
| 2008/0065758 | A1 | * | 3/2008  | Narayanaswami .......... 709/224 |

OTHER PUBLICATIONS

Matt Jensen and NewsBlip—"Visualizing Complex Semantic Timelines"—dervied from the world wide web; http://newsblip.com 2003 pp. 1-3 (citeseer.*
Pierre Wellner, Mike Flynn and Mael Guillemot—"Browsing recordings of Multi-party Interactions in Ambient Intelligent Environments"—Proc. CHI Workshop Lost in Ambient, 2004 Citeseer (pp. 1-30.*

* cited by examiner

*Primary Examiner*—Jean B. Fleurantin
*Assistant Examiner*—Anh Ly
(74) *Attorney, Agent, or Firm*—Park, Vaughan & Fleming LLP; Anthony P. Jones

(57) ABSTRACT

Embodiments of the present invention provide a system that tracks progress on a plan. The system starts by receiving a one or more completed plan templates (which constitute plans) from a set of plan providers. The system then stores the plans in a plan database. Next, the system receives a request for a plan, for which the plan database contains one or more plans that can be used to fulfill the request. The system then provides a user interface (UI) to display the plans that fulfill the request. Next, the system receives a selection signal that selects a plan to fulfill the request. The system then displays the selected plan through the UI, which involves initially displaying projected progress on the plan at one or more intervals on a timeline.

31 Claims, 4 Drawing Sheets
(1 of 4 Drawing Sheet(s) Filed in Color)

PROGRESS-TRACKING SERVICE

BACKGROUND

1. Field of the Invention

Embodiments of the present invention relate to techniques for tracking progress. More specifically, embodiments of the present invention relate to a technique for using a progress-tracking service to keep track of progress which is made while following a plan.

2. Related Art

Many plans require a person to carefully keep track of recommended actions and the associated results. One example of such a plan is a weight-loss plan, which has carefully structured dietary requirements, exercise requirements, and weight goals. Another example is a body-building plan, which can include dietary requirements, performance benchmarks, and detailed exercise and rest requirements. Another example is healthcare plans (e.g., chemotherapy plans, drug trials, or surgery recovery plans), which may include daily drug dosage times and amounts, physical therapy recommendations, vital statistics tracking, and corresponding progress indicators. Yet another example is financial plans, which can include spending constraints, savings targets, and ultimate goals.

Some websites on the Internet facilitate tracking such plans. For example, some diet-planning companies provide websites that permit a person following the plan to determine the plan's requirements for a given day and to enter that day's event information and progress indicators (e.g., amount of calories consumed in a given day and daily measured weight).

Unfortunately, these websites are typically designed to allow the tracking of one specific plan. Moreover, each website has its own layout and presentation format. The individualized nature of the different plan tracking websites can make it difficult for a consumer to compare plans and to decide which plan is best for their needs. In addition, tracking progress while switching from one plan to another can be difficult because of the differences in these websites.

SUMMARY

Embodiments of the present invention provide a system that tracks progress on a plan. The system starts by receiving a one or more completed plan templates (which constitute plans) from a set of plan providers. The system then stores the plans in a plan database. Next, the system receives a request for a plan, for which the plan database contains one or more plans that can be used to fulfill the request. The system then provides a user interface (UI) to display the plans that fulfill the request. Next, the system receives a selection signal that selects a plan to fulfill the request. The system then displays the selected plan through the UI, which involves initially displaying projected progress on the plan at one or more intervals on a timeline.

In some embodiments, the system receives a progress update for an interval on the timeline. The system then uses the UI to display the received progress update for the interval on the timeline and to display the projected progress for any intervals on the timeline which have not been updated with progress updates.

In some embodiments, the UI includes: (1) a timeline element that displays the timeline; (2) a summary element that displays a summary of progress while following the selected plan; and (3) an information element that displays information about the selected plan.

In some embodiments, the timeline element displays only a portion of the intervals available on the timeline. In these embodiments, the timeline can be scrolled in one direction to display earlier time intervals or in the opposite direction to display later time intervals.

In some embodiments, the information element is associated with the timeline so that the information element displays information about the intervals displayed in the timeline. In these embodiments, the system updates the information displayed in the information element to match the intervals displayed in the timeline as the timeline is scrolled.

In some embodiments, when receiving a progress update for an interval on the timeline, the system receives: a manually-entered update, an update in an email, an update in a text message, and/or an update from another application.

In some embodiments, the plan is a diet plan, a fitness plan, a healthcare plan, a financial plan, or another type of plan that includes a set of recommendations for actions and a set of associated results.

In some embodiments, the system generates a message to indicate the plan events that are to occur in a given interval on the timeline. The system then delivers the message through the UI, an email, a text message, and/or another message format.

In some embodiments, the system receives a command to post a copy of some or all of the UI to a website. The system then posts a copy of some or all of the UI to the website.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

DETAILED DESCRIPTION

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the claims.

The data structures and code described in this detailed description are typically stored on a computer-readable storage medium, which may be any device or medium that can store code and/or data for use by a computer system.

This includes, but is not limited to, magnetic and optical storage devices, such as disk drives, magnetic tape, CDs (compact discs) and DVDs (digital versatile discs or digital video discs), or solid-state devices, such as flash memory, or other volatile and non-volatile storage mediums.

Computer System

Figure 1:
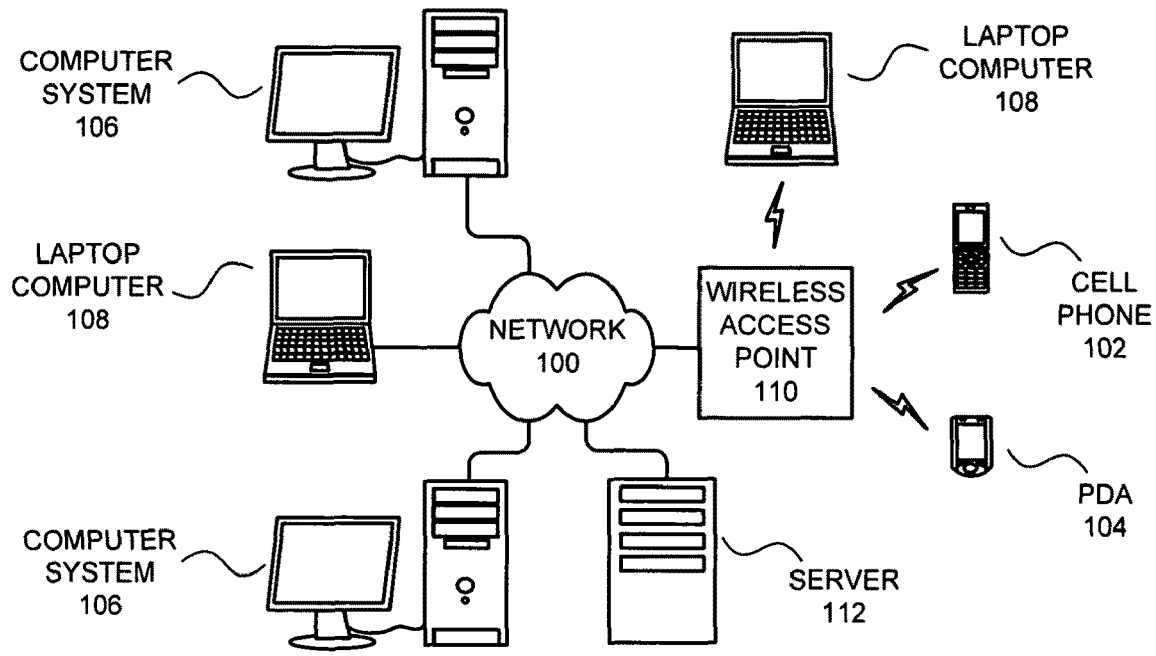
FIG. 1 presents a set of network nodes coupled to a network in accordance with embodiments of the present invention.

FIG. 1 presents a set of network nodes coupled to network 100 in accordance with embodiments of the present invention. Network 100 can generally include any type of wired or wireless communication channel capable of coupling together network nodes. This includes, but is not limited to, a local area network, a wide area network, or a combination of networks. In some embodiments of the present invention, the network includes the Internet.

Network nodes can generally include any type of communication device capable of communicating with other network nodes via a communication network. This includes, but is not limited to, a computer system 106, a server 112, a laptop computer 108, a wireless access point 110, a cell phone 102, or a personal digital assistant (PDA) 104. Although a particular combination of networks and network nodes is shown in FIG. 1, alternative embodiments of the present invention can use different combinations of networks and network nodes.

A network node can use network 100 exchange data with other network nodes. For example, cell phone 102 may be able to acquire web pages and messages from server 112 or may be able to receive email messages from laptop computer 108. In another example, computer system 106 may be able to store web pages and data on server 112, which can then be read by other network nodes.

Server 112 or another host computing device coupled to network 100 can host a web log ("blog"). Generally, a blog is hosted by a website where the blog's author can add entries to provide information, commentary, and/or news on a subject such as food, politics, business practices, or any of a large number of subjects. Some blogs function as personal website-based "diaries" or "journals," where authors enter text, images, video, audio, or other forms of media to provide information, commentary, or news about their personal lives. A user can use a network node (such as laptop computer 108) to edit an entry for a blog. The user can then upload the blog entry to the host computing device for others to download and read.

In some embodiments of the present invention, a progress-tracking service 200 (see FIG. 2) application runs on server 112 (or another suitable network node). Generally, progress-tracking service 200 can provide vendors, individuals, and/or organizations (collectively "plan providers") with plan templates, which the plan providers can fill in with the details of their corresponding plan(s), which the plan providers then return to progress-tracking service 200. Progress-tracking service 200 then stores the plans (i.e., the populated plan templates) in a plan database. When a client 208 requests a particular type of plan, progress-tracking service 200 determines which plans in the plan database will work for the client and generates a corresponding UI 300 (see FIG. 3A) to display the plans. Progress-tracking service 200 then displays the UI 300 including the plans to client 208. Using UI 300, client 208 compares the plans from the different plan providers. This allows client 208 to select a plan and to track progress while following the selected plan. Because the plan providers fill in the details in a plan template, a client 208 can more easily compare plans from different plan providers and can switch between plans more easily.

In some embodiments of the present invention, client 208 can publish some or all of UI 300 in a blog for other users to read and comment on. For example, a client 208 using computer system 106 can track progress in UI 300 and can optionally publish UI 300 in a blog hosted by server 112 or another host. If published, the blog entry can be downloaded and read by another user, for example on PDA 104 or on laptop computer 108.

Progress-Tracking System

Generating and Using Plan Templates

Figure 2:
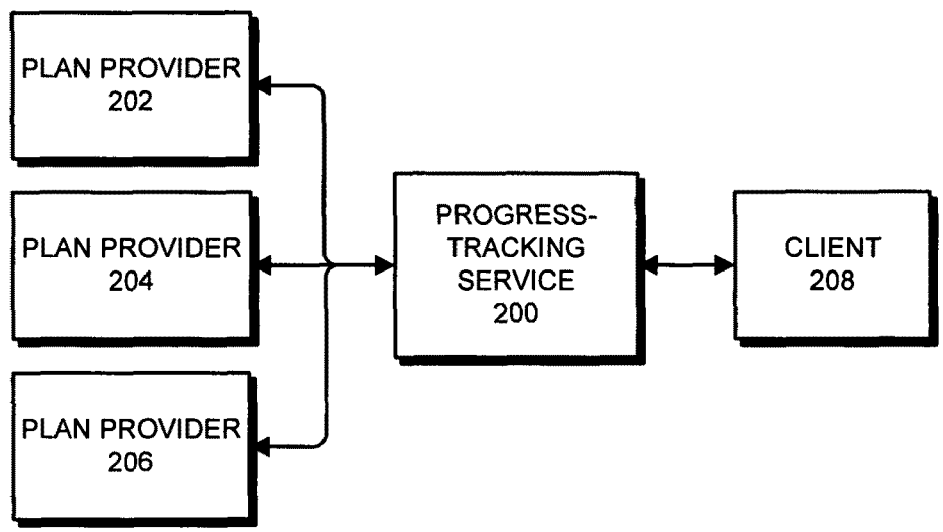
FIG. 2 presents a block diagram of a progress-tracking system in accordance with embodiments of the present invention.

FIG. 2 presents a block diagram of a progress-tracking system in accordance with embodiments of the present invention. The progress-tracking system allows client 208 to compare plans, select a plan to follow, and track progress on the selected plan. The progress-tracking system includes progress-tracking service 200, plan providers 202-206, and client 208.

Progress-tracking service 200 includes a number of plan templates. For example, plan templates can include diet plan templates, fitness plan templates, financial plan templates, healthcare plan templates, newborn baby plan templates, drug trial plan templates, school curriculum templates, construction plan templates, business method implementation plan templates, project schedule templates, new software release templates, gardening plan templates, or other plan templates.

In some embodiments of the present invention, each plan template includes a one or more entries for actions to be taken ("action-entries") and one or more entries for the projected results of those actions ("result-entries"). For example, a diet plan template can include a set of action-entries for recommended daily caloric intake and exercise, and a corresponding set of result-entries the projected weight losses. Alternatively, a construction plan template can include a series of action-entries for cost of materials and labor for a construction project, and corresponding result-entries for the projected completion stages of the project. Note that we present plan templates with "action" and "result" entries for the purposes of illustration, but, in alternative embodiments, plan templates can include other types of entries that can be used to help compare plans and/or track progress while following a plan.

A plan provider 202 acquires a plan template from progress-tracking service 200 and fills in the entries in a plan template with the details of their corresponding plan. For example, a financial institution can upload a retirement plan template and can fill in the "actions" entries in the retirement plan template with savings amounts and asset allocations at different times during a client's life and the "results" entries with the predicted savings amounts. When the entries are populated, the plan provider 202 returns the completed plan template to the progress-tracking service 200. For example, the financial institution can upload the retirement plan template to progress-tracking service 200 using network 100.

In some embodiments of the present invention, within the "actions" and "results" entries, the plan templates provide space for the plan provider to insert text, images, audio, video, web links, file names, and other information that helps a client 208 determine what actions are required and what results can be expected. Generally, the plan template can include UI graphics (i.e., text, images, video, etc.) and audio, metadata defining content to be captured, content for a help UI, and other content.

Progress-tracking service 200 adds the completed plan template to a plan database. In some embodiments of the present invention, progress-tracking service 200 can collect separate completed plan templates from multiple plan providers for each type of plan. For example, progress-tracking service 200 can collect completed diet plan templates from diet plan providers such as Weight Watchers™, The South Beach Diet™, Jenny Craig™, etc. Alternatively, progress-tracking service can collect completed retirement plan templates from Edward Jones™, Fidelity™, private certified financial planners (CFP), etc.

When trying to decide on a plan to follow in order to achieve a particular goal, client 208 can request a set of plans to review from progress-tracking service 200. For example, client 208 may request diet plans or financial plans from progress-tracking service 200. In response, progress-tracking service 200 assembles a set of plans from the completed plan templates. Generally, the assembled set of plans includes as many plans as possible that relate to client 208's request. For example, if a doctor requests a physical therapy plan for a patient, progress-tracking service 200 can assemble several physical therapy plans from different medical providers.

Progress-tracking service 200 then creates a UI 300 (see FIG. 3A) for presenting the assembled plan templates to the client 208 and provides the UI to the client 208. In some embodiments of the present invention, client 208 downloads UI 300 from progress-tracking service 200 in the form of a web page on the Internet.

User Interface

Figure 3A:
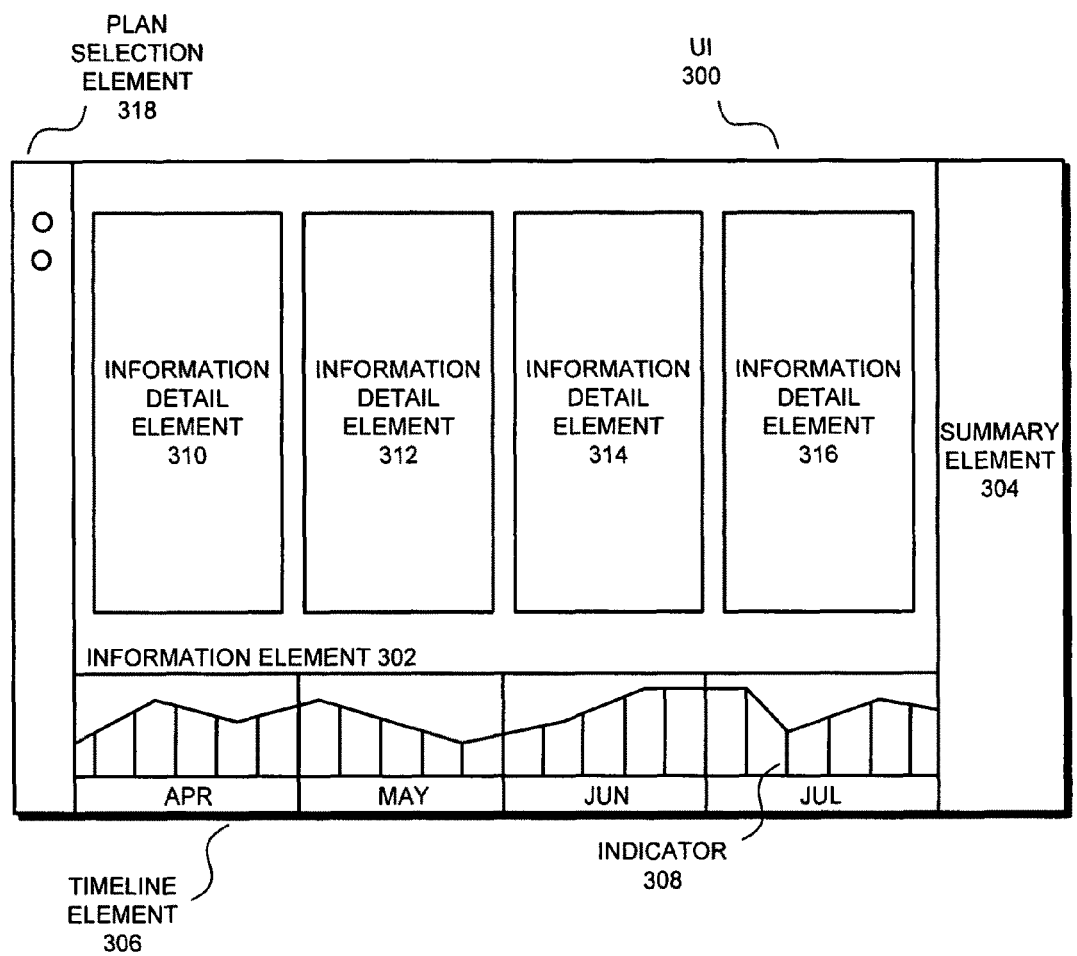
FIG. 3A illustrates an exemplary UI provided for a progress-tracking service in accordance with embodiments of the present invention.

FIG. 3A illustrates an exemplary UI 300 provided by progress-tracking service 200 in accordance with embodiments of the present invention. A client 208 can use UI 300 to compare different plans, to select a plan from among two or more different plans, and/or to review current/past progress and/or estimations of future progress while subsequently following a selected plan.

In some embodiments of the present invention, UI 300 includes information element 302, summary element 304, timeline element 306, and plan-selection element 318. Timeline element 306 displays a timeline of plan progress. Generally, the timeline is scaled according to the requirements of the plan. For example, assuming that the plan is a weekly fitness plan, the timeline can be scaled to represent a series of weeks. On the other hand, assuming that the plan is a long-term financial plan, the timeline can be scaled to represent a series of months or years.

In some embodiments of the present invention, UI 300 provides one or more indicators 308 of plan progress on the timeline. Depending on what data is available, the indicators 308 can represent measured values or projections of progress (i.e., projections can be used where measured data is not available). For example, assuming that the plan is a diet plan where timeline element 306 shows a client 208's weight on a daily basis, the timeline can include indicators 308 that represent measured weight values (i.e., where those values have been entered), as well as indicators 308 that represent projections of weight values.

In some embodiments of the present invention, the indicators 308 can be arrows or other graphics which visually indicate the performance of the plan for the given indicator 308. For example, assuming that the plan is a financial plan, an arrow pointing downward for a given indicator 308 can indicate that the client 208 did not save as much as the plan recommended.

In some embodiments of the present invention, timeline element 306 displays only a portion of the entire timeline. For example, timeline element 306 may be configured to display 3 weeks out of a timeline for a 10-week plan. In these embodiments, the client 208 can use a mouse pointer or another suitable control to scroll (e.g., click-and-drag) the timeline to the left or right to display other portions of the timeline. For example, if timeline element 306 is displaying weeks 3-5 of a 10-week plan, the client 208 can drag the timeline to the left to display weeks 6-8 or 7-9, or drag the timeline to the right to display weeks 1-2.

In some embodiments of the present invention, information element 302 provides the client 208 with information related to a plan. Information element 302 includes information detail elements 310-316. Each information detail element can include information associated with a given plan timeline interval, such as text, audio, images, video, links to web pages or files, or other information. For example, as shown in FIG. 3, information detail element 310 can contain information corresponding to the month of April, while the other information detail elements contain information corresponding to the other months in the timeline. More specifically, assuming that the plan shown in UI 300 is a vegetable gardening plan, each information detail element may provide a description of plant height and vegetable development, as well a recommendation for hours of sunlight, temperatures, fertilizer amounts, and watering amounts for a corresponding month.

In some embodiments of the present invention, the information detail elements are updated as the timeline is scrolled to the left or right. In other words, the horizontal axis (i.e., the timeline) becomes the standard axis for viewing plan progress information. For example, a 10-week diet plan may have a timeline that is divided into weeks, each week with a corresponding information detail element, and these information detail elements can be displayed in when the corresponding timeline segment is displayed.

In some embodiments of the present invention, summary element 304 provides the client 208 with summary information about plan progress and/or plan projections. For example, assuming that the plan is a financial plan, the summary element can provide the client 208 with summary return on investment information and summary projections for returns in the overall investing period.

Figure 3B:
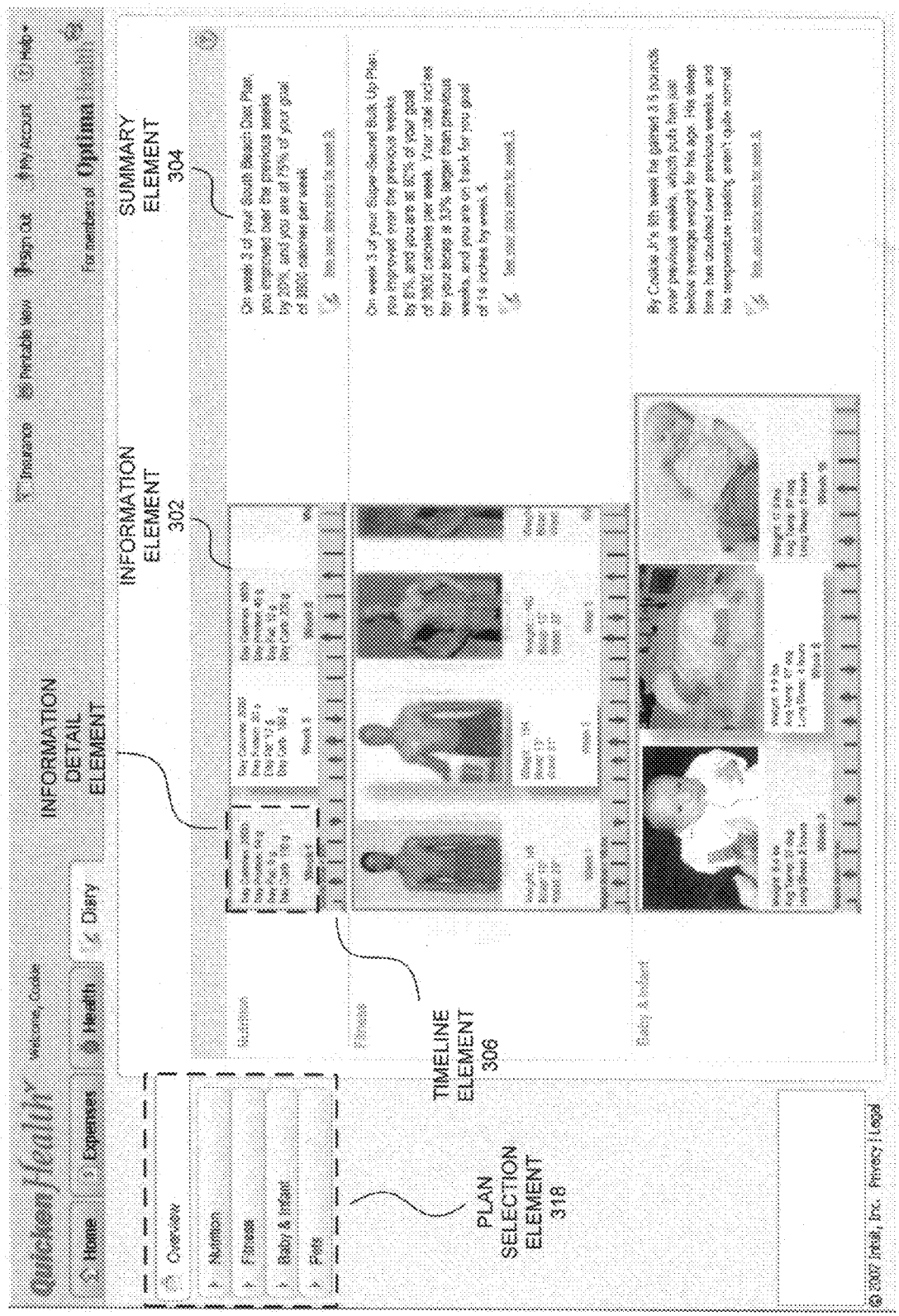
FIG. 3B presents an overview UI in accordance with embodiments of the present invention.

FIG. 3B presents an overview UI in accordance with embodiments of the present invention. The overview UI is configured to display several plan summaries: a nutrition plan summary, a fitness plan summary, and a baby & infant plan summary. As with UI 300, each of the plan summaries includes timeline element 306, information element 302, and summary element 304. Information element 302 includes a set of information detail elements that are associated with the corresponding timeline element 306. For example, the nutrition plan summary includes information detail elements for weeks 1, 3, and 5 and the timeline element corresponding to the information detail element.

In some embodiments of the present invention, the elements for each plan summary in the overview UI function in the same way as the corresponding elements in UI 300. For example, the timeline displayed in timeline element 306 can be scrolled and the information element 302 will be updated to display the corresponding information detail elements. In an alternative embodiment, one or more of the elements may have reduced functionality (e.g., the timeline may not be scrollable).

FIG. 3B also includes plan selection element 318. Plan selection element 318 allows users to select the overview UI (i.e., the UI that is currently selected in FIG. 3B) or a UI 300 for each plan. For example, the user can select the baby & infant plan, which switches the UI to view a UI 300 that includes an expanded view of the baby & infant plan.

Comparing Plans and Selecting a Plan

In some embodiments of the present invention, information element 302 can display information for two or more plans to a client 208. For example, if progress-tracking service 200 has two or more completed plan templates that meet a client's request, progress-tracking service 200 can provide multiple plan templates in UI 300.

In some embodiments of the present invention, UI 300 displays information about only one plan, but client 208 can alternate between the displayed plans using plan-selection element 318. For example, if progress-tracking service 200 creates a UI 300 that display information for a Weight Watchers™ plan and a South Beach Diet™ plan, only the details of one of the diet plans is displayed at a time, but client 208 can use plan-selection element 318 to switch UI 300 to display the other retirement plans (one at a time).

In some embodiments of the present invention, UI 300 can display information about multiple plans simultaneously. In other words, each information detail element 210-216 can include separate information such as text, audio, images, video, links to web pages or files, or other information for two or more plans. For example, information element 302 can display information for a Weight Watchers plan and a South Beach Diet plan. In this case, each information detail element displays information about the diet corresponding to a timeline interval (e.g., monthly dietary recommendations and weight loss projections).

In both embodiments, client 208 can select a plan from among the two or more plans and the progress-tracking service 200 will update the elements in UI 300 to display details related to the selected plan. For example, if the client 208 selects a South Beach Diet plan, the information element 302, summary element 304, and timeline element 306 are updated to correspond to the South Beach Diet.

After comparing plans in UI 300 and determining that a particular plan meets their needs, client 208 can select the plan. After selecting the plan, the client 208 can use UI 300 to track their progress on the plan (as described below).

Note that the client 208 can change the selected plan at any time. For example, the client 208 can select the South Beach Diet based on projected weight loss and then switch to the Weight Watchers Diet if the South Beach Diet does not prove to be satisfactory (e.g., if the weight loss projections prove to be inaccurate). In this case, the information element 302, the timeline element 306, and the summary element 304 are updated using available metrics from the prior plan (e.g., the earlier measured weight loss on the South Beach Diet plan can be used when generating the projection(s) of weight loss on the Weight Watchers plan).

Note that in some embodiments of the present invention, only one plan is presented to client 208. For example, if a personal trainer has assembled a customized fitness program, there may be no other plans to which the plan can be compared. In this case, client 208 may not need to "select" the plan, as the plan is the only available plan.

Tracking Progress on a Selected Plan

After selecting a, client 208 commences following the plan. For example, assuming that the plan is a diet plan, client 208 begins to follow the recommendations (as presented within UI 300) for caloric intake and exercise.

While following a plan, a client or another entity can provide an update of progress to the progress-tracking service 200. For example, assuming that the plan is for a drug trial, a test-subject, a lab technician, a doctor, or another person involved with the testing can provide weekly measurement values of vital signs (such as blood pressure, weight, heart rate, etc.) for the test-subject. Alternatively, assuming that the plan is a retirement plan, the client 208 or the client's financial advisor or financial institution can provide monthly savings amounts and types.

In embodiments of the present invention, the client 208 (or other entity) can manually input progress updates. Alternatively, in some embodiments of the present invention, the progress updates can be received or gathered automatically. For example, assuming that the plan is a financial plan, a monthly electronic statement can be gathered or received from a financial institution (and then the information included in the statement can be used to generate a progress update).

In some embodiments of the present invention, client 208 or another entity can provide progress updates using a text message, an email, or another type of electronic message. For example, a client can send a formatted text message using cell phone 102 or PDA 104.

When a client or another entity has provided a progress update, the progress-tracking service 200 stores the update in a database. For example, the progress-tracking service 200 can store a client's vital signs updates in a database entry associated with the client 208.

In some embodiments of the present invention, progress-tracking service 200 generates updated projections of future progress after receiving each progress update. The progress-tracking service 200 then displays the updated projections in UI 300. For example, assuming that a client is on week three of an eight-week diet plan, the actual results (i.e., weight and body-fat measurements) entered in prior weeks can be used in combination with the updates in the current week to project the results over the remaining weeks of the plan.

In some embodiments of the present invention, a message is sent to client 208 to inform client 208 of a set of plan recommendations or requirements. For example, assuming that the plan is a bodybuilding plan, client 208 can be sent an email or a text message to inform client 208 of caloric-intake and exercise/rest requirements for a given day or week.

Publishing the UI on the Internet

In some embodiments of the present invention, progress-tracking service 200 includes a blogging mechanism which facilitates a client "publishing" some or all of UI 300 in a blog. The blog's readers can then download the blog entry and read and comment on it.

The copy of UI 300 in the blog entry can be used by the blog reader in the same way as the original copy. For example, the blog reader can scroll the timeline to show unseen portions of the timeline (and information element 302 will be updated accordingly).

In some embodiments, two or more clients 208 (i.e., blog publishers) can combine their plan progress information. The clients 208 can place the combined plan progress information into a single UI 300 and then publish the combined information in a blog entry.

In some embodiments of the present invention, progress-tracking service 200 can post some or all of UI 300 on a website other than a blog. For example, a client 208 may publish some or all of a retirement plan to a personal or commercial website for others to view.

Following a Plan

Figure 4:
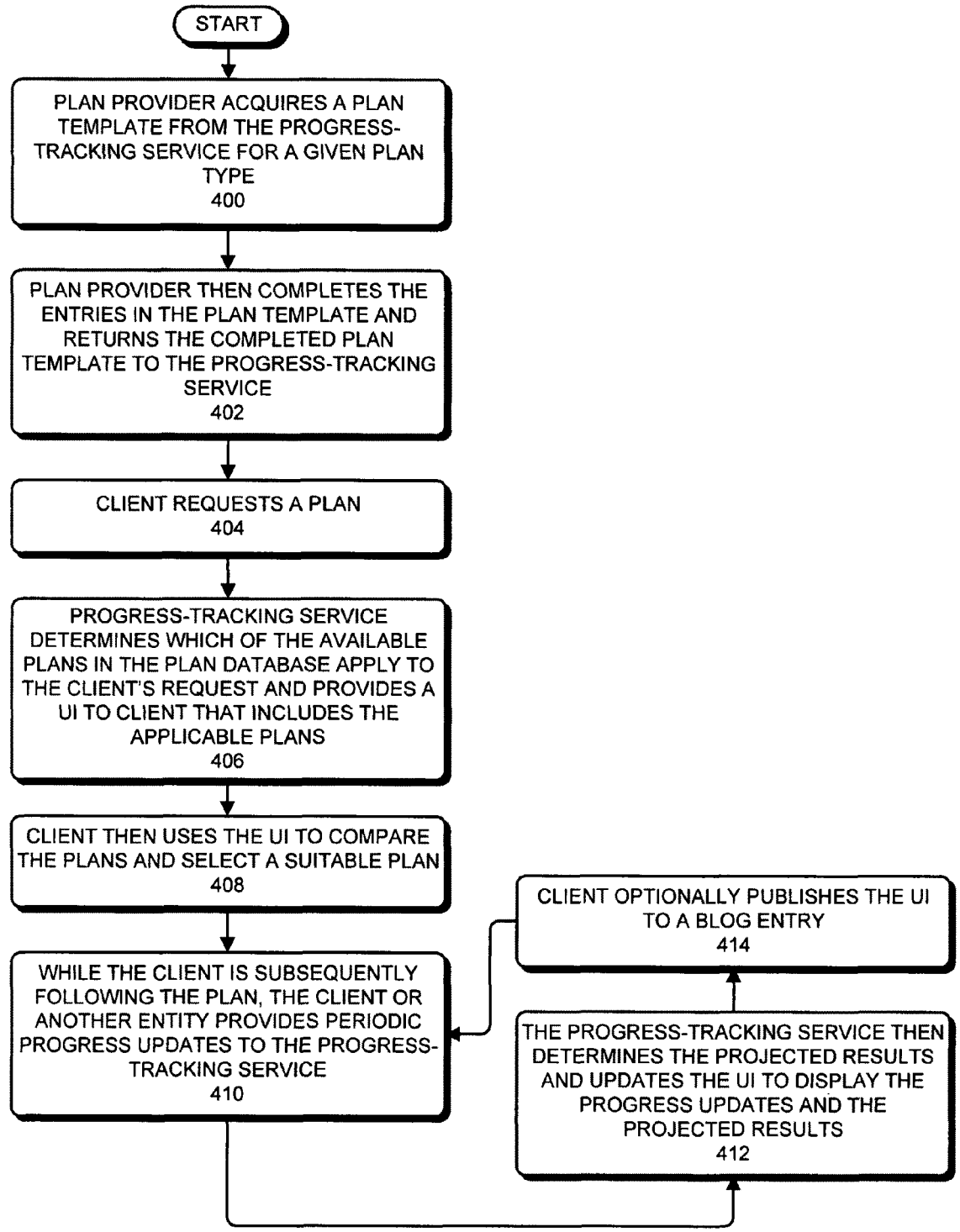
FIG. 4 presents a flowchart illustrating the process of selecting and tracking a plan in accordance with embodiments of the present invention.

FIG. 4 presents a flowchart illustrating the process of selecting and tracking a plan in accordance with embodiments of the present invention. The process starts when a plan provider 202 acquires a plan template from the progress-tracking service 200 for a given plan type (step 400). For example, a personal trainer can download a "fitness" or a "bodybuilding" plan template.

The plan provider then completes the entries in the plan template and returns the completed plan template ("plan") to progress-tracking service 200 (step 402). In some embodiments of the present invention, when completing the entries in the plan template, plan provider 202 provides a series of "actions" to be taken by a client 208 and a set of "results" that arise from taking the actions. The entries in the plan template may include text, graphics, video, audio, web links, filenames, and other information that can help in selecting a plan and following the plan. For example, assuming that the plan template is the fitness plan template, within each entry the personal trainer can provide a set of daily diet and exercise recommendations that includes images of a person who has followed the fitness plan, as well as audio and/or video explaining the daily diet and exercise recommendations. Upon receiving the plan, progress-tracking service 200 stores the plan in a plan database.

More than one plan provider 202 can fill in a given plan template to provide plans to progress-tracking service 200. As each plan provider 202 provides plans to progress-tracking service 200, progress-tracking service 200 stores the plans in the plan database.

A client 208 then requests a plan (step 404). For example, client 208 can request a fitness plan. In some embodiments of the present invention, client 208 can provide personalized information along with the request for the plan. For example, a client 208 requesting a fitness plan may include information about weight, age, and current fitness level. Progress-tracking service 200 can then consider this information (in step 406) when determining which of the available plans apply to the client's request.

Next, progress-tracking service 200 determines which of the available plans in the plan database apply to the client's request and provides a UI 300 to client 208 that includes the applicable plans (step 406). For example, if the progress-tracking service 200 has received other fitness plans, the progress-tracking service 200 generate a UI 300 that includes the fitness plans. (If there is only one fitness plan available in the database, the progress-tracking service 200 generates a UI 300 that includes only the one fitness plan.)

The client 208 then uses the UI 300 to compare the plans and select a suitable plan (step 408). (Note that this step is optional where only one plan is provided with UI 300.) When client 208 has selected the plan, UI 300 is updated to show projected results for a client who is following the selected plan. For example, if the plan is a fitness plan, information element 302, summary element 304, and timeline element 306 can be updated to show projected body mass gains and body-fat content.

While client 208 is subsequently following the plan, client 208 (or another entity) provides progress updates to the progress-tracking service 200 (step 410). For example, while following a fitness plan, client 208 can measure body mass and body-fat content on a weekly basis and can provide these measurements to the progress-tracking service 200. Progress-tracking service 200 stores the updates in a database associated with the client 208 and the plan that the client is following.

Progress-tracking service 200 then determines the projected results and updates the UI 300 to display the progress updates and the projected results (step 412). For example, if the plan is a fitness plan, the progress-tracking service 200 can project future body-fat contents and mass gains. Progress-tracking service 200 can then update the UI to show the past and current actual measurements and the updated projections.

Client 208 can then optionally publish the UI 300 (step 414). For example, the client can publish the UI 300 in a blog entry or on another type of webpage on the Internet. When the client has published the UI in a blog entry, the blog's readers can read and comment on the entry.

The foregoing descriptions of embodiments of the present invention have been presented only for purposes of illustration and description. They are not intended to be exhaustive or to limit the present invention to the forms disclosed. Accordingly, many modifications and variations will be apparent to practitioners skilled in the art. Additionally, the above disclosure is not intended to limit the present invention. The scope of the present invention is defined by the appended claims.

What is claimed is:

1. A method for tracking progress on a plan, comprising:
    receiving a request for a plan from a client, wherein a plan database contains one or more plans that can be used to fulfill the request;
    providing a user interface (UI) to display the plans that fulfill the request, wherein the UI displays:
    a timeline element which displays the timeline;
    a summary element which displays a summary of progress while following the selected plan; and
    an information element that displays information which is associated with the timeline and displays information about intervals displayed in the timeline;
    updating the information displayed in the information element to match the intervals displayed in the timeline as the timeline is scrolled;
    receiving a selection signal that selects a plan to fulfill the request;
    receiving a progress update for the client for the selected plan; and
    displaying the selected plan through the UI, which involves using the progress update to display projected progress for the client while following the selected plan.

2. The method of claim 1, wherein the projected progress is displayed at one or more intervals on a timeline and wherein the method further comprises:
    receiving a progress update for an interval on the timeline; and
    using the UI to display the received progress update for the interval on the timeline and to display the projected progress for any intervals on the timeline which have not been updated with progress updates.

3. The method of claim 2, wherein receiving the progress update for the interval on the timeline involves receiving: a manually-entered update, an update in an email, an update in a text message, and/or an update from another application.

4. The method of claim 2, wherein the method further comprises generating a message to indicate the plan events that are to occur in a given interval on the timeline and delivering the message using the UI, an email, a text message, and/or another message format.

5. The method of claim 1, wherein the method further comprises: receiving a one or more completed plan templates which constitute plans from a set of plan providers; and
    storing the plans in the plan database.

6. The method of claim 1, wherein the timeline element displays only a portion of the intervals available on the timeline, and wherein the timeline can be scrolled in one direction to display earlier time intervals or in the opposite direction to display later time intervals.

7. The method of claim 1, wherein the method further comprises:
   receiving a command to post a copy of some or all of the UI to a website; and
   posting a copy of some or all of the UI to the website.

8. The method of claim 1, wherein the plan is: a diet plan, a fitness plan, a healthcare plan, a financial plan, or another type of plan that includes a set of recommendations for actions and a set of associated results.

9. A computer-readable storage medium that contains instructions that when executed by a computer cause the computer to perform a method for tracking progress on a plan, the method comprising:
   receiving a request for a plan from a client, wherein a plan database contains one or more plans that can be used to fulfill the request;
   providing a user interface (UI) to display the plans that fulfill the request,
   providing a user interface (UI) to display the plans that fulfill the request,
   wherein the UI displays:
   a timeline element which displays the timeline;
   a summary element which displays a summary of progress while following the selected plan; and
   an information element that displays information which is associated with the timeline and displays information about intervals displayed in the timeline;
   updating the information displayed in the information element to match the intervals displayed in the timeline as the timeline is scrolled;
   receiving a selection signal that selects a plan to fulfill the request;
   receiving a progress update for the client for the selected plan; and displaying the selected plan through the UI, which involves using the progress update to display projected progress for the client while following the selected plan.

10. The computer-readable storage medium of claim 9, wherein the projected progress is displayed at one or more intervals on a timeline and wherein the method further comprises:
    receiving a progress update for an interval on the timeline; and
    using the UI to display the received progress update for the interval on the timeline and to display the projected progress for any intervals on the timeline which have not been updated with progress updates.

11. The computer-readable storage medium of claim 10, wherein receiving the progress update for the interval on the timeline involves receiving: a manually-entered update, an update in an email, an update in a text message, and/or an update from another application.

12. The computer-readable storage medium of claim 10, wherein the method further comprises generating a message to indicate the plan events that are to occur in a given interval on the timeline and delivering the message using the UI, an email, a text message, and/or another message format.

13. The computer-readable storage medium of claim 9, wherein the method further comprises:
    receiving a one or more completed plan templates which constitute plans from a set of plan providers; and
    storing the plans in the plan database.

14. The computer-readable storage medium of claim 9, wherein the timeline element displays only a portion of the intervals available on the timeline, and wherein the timeline can be scrolled in one direction to display earlier time intervals or in the opposite direction to display later time intervals.

15. The computer-readable storage medium of claim 9, wherein the method further comprises:
    receiving a command to post a copy of some or all of the UI to a website; and
    posting a copy of some or all of the UI to the website.

16. The computer-readable storage medium of claim 9, wherein the plan is: a diet plan, a fitness plan, a healthcare plan, a financial plan, or another type of plan that includes a set of recommendations for actions and a set of associated results.

17. An apparatus for tracking progress on a plan, comprising:
    a request-receiving mechanism that receives a request for a plan from a client, wherein a plan database contains one or more plans that can be used to fulfill the request;
    a user interface (UI) mechanism configured to display the plans that fulfill the request, providing a user interface (UI) to display the plans that fulfill the request, wherein the UI displays:
    a timeline element which displays the timeline;
    a summary element which displays a summary of progress while following the selected plan; and
    an information element that displays information which is associated with the timeline and displays information about intervals displayed in the timeline;
    updating the information displayed in the information element to match the intervals displayed in the timeline as the timeline is scrolled;
    a selection mechanism that receives a selection signal that selects a plan to fulfill the request; and
    an update mechanism that receives a progress update for the client for the selected plan;
    wherein the UI displays the selected plan, which involves using the progress update to display projected progress for the client while following the selected plan.

18. The apparatus of claim 17, wherein the UI displays the projected progress at one or more intervals on a timeline, wherein the apparatus further comprises:
    a progress-update mechanism that receives a progress update for an interval on the timeline; and
    wherein the UI mechanism displays the received progress update for the interval on the timeline and displays the projected progress for any intervals on the timeline which have not been updated with progress updates.

19. The apparatus of claim 18, wherein receiving the progress update for the interval on the timeline involves receiving: a manually-entered update, an update in an email, an update in a text message, and/or an update from another application.

20. The apparatus of claim 18, further comprising a message-generation mechanism that generates a message to indicate the plan events that are to occur in a given interval on the timeline and delivers the message using the UI, an email, a text message, and/or another message format.

21. The apparatus of claim 17, further comprising a plan-receiving mechanism that receives a one or more completed plan templates which constitute plans from a set of plan providers and stores the plans in a plan database.

22. The apparatus of claim 17, wherein the UI mechanism is configured so that the timeline element displays only a portion of the intervals available on the timeline, and so that the timeline is scrolled in one direction to display earlier time intervals or in the opposite direction to display later time intervals.

23. The apparatus of claim 17, further comprising a publishing mechanism that is configured to post a copy of some or all of the UI to a website upon receiving a posting request.

24. The apparatus of claim 17, wherein the plan is: a diet plan, a fitness plan, a healthcare plan, a financial plan, or another type of plan that includes a set of recommendations for actions and a set of associated results.

25. A client system for tracking progress on a plan, comprising:
- a processor;
- memory;
- a display mechanism;
- a requesting mechanism for requesting plans from a plan-tracking service, wherein the display mechanism displays a UI that includes plans returned from the plan-tracking service, providing a user interface (UI) to display the plans that fulfill the request, wherein the UI displays:
- a timeline element which displays the timeline;
- a summary element which displays a summary of progress while following the selected plan; and
- an information element that displays information which is associated with the timeline and displays information about intervals displayed in the timeline;
- updating the information displayed in the information element to match the intervals displayed in the timeline as the timeline is scrolled;
- an update mechanism for receiving a progress update for the client for the selected plan; and
- a selection mechanism for selecting a plan from the plans returned from the plan tracking service, wherein the display mechanism displays a UI that includes the selected plan, which involves using the progress update to display projected progress for the client while following the selected plan at one or more intervals on a timeline.

26. The client system of claim 25, further comprising a progress-update mechanism for receiving a progress update for an interval on the timeline, wherein the display mechanism displays the received progress update for the interval on the timeline and displays the projected progress for any intervals on the timeline which have not been updated with progress updates.

27. The client system of claim 26, wherein when receiving the progress update for the interval on the timeline, the progress-update mechanism is configured to receive: a manually-entered update, an update in an email, an update in a text message, and/or an update from another application.

28. The client system of claim 25, wherein the display mechanism is configured so that the timeline element displays only a portion of the intervals available on the timeline, and so that the timeline is scrolled in one direction to display earlier time intervals or in the opposite direction to display later time intervals.

29. The client system of claim 25, further comprising a publishing mechanism for posting a copy of some or all of the UI to a website.

30. The client system of claim 25, wherein the plan is a diet plan, a fitness plan, a healthcare plan, a financial plan, or another type of plan that includes a set of recommendations for actions and a set of associated results.

31. The client system of claim 25, further comprising a message-generation mechanism that generates a message to indicate the plan events that are to occur in a given interval on the timeline and delivers the message using the UI, an email, a text message, and/or another message format.

* * * * *

UNITED STATES PATENT AND TRADEMARK OFFICE
CERTIFICATE OF CORRECTION

PATENT NO. : 7,774,324 B2 Page 1 of 1
APPLICATION NO. : 11/888104
DATED : August 10, 2010
INVENTOR(S) : Kenneth Henderson et al.

It is certified that error appears in the above-identified patent and that said Letters Patent is hereby corrected as shown below:

In claim 9 (at column 11, lines 19-20), please delete the duplicate lines:
"providing a user interface (UI) to display the plans that fulfill the request,".

Signed and Sealed this

Sixteenth Day of November, 2010

David J. Kappos
*Director of the United States Patent and Trademark Office*